US00PP23578P2

(12) United States Plant Patent
Richards et al.

(10) Patent No.: US PP23,578 P2
(45) Date of Patent: Apr. 30, 2013

(54) ***SALVIA* PLANT NAMED 'AMISTAD'**

(50) Latin Name: ***Salvia* hybrid**
Varietal Denomination: Amistad

(76) Inventors: Rodney W. Richards, Hereford (GB); Rolando Aníbal Uría, Lanús (AR)

( * ) Notice: Subject to any disclaimer, the term of this patent is extended or adjusted under 35 U.S.C. 154(b) by 114 days.

(21) Appl. No.: 13/136,695

(22) Filed: Aug. 8, 2011

(51) Int. Cl.
*A01H 5/00* (2006.01)

(52) U.S. Cl. ..... Plt./475

(58) Field of Classification Search ..... Plt./475
See application file for complete search history.

*Primary Examiner* — June Hwu
(74) *Attorney, Agent, or Firm* — Penny J. Aguirre

(57) ABSTRACT

A new cultivar of hybrid *Salvia*, 'Amistad' characterized by its flowers that are mauve purple in color, its blooms that commences early in the season, its long blooming habit with new shoots producing flowers throughout the summer, its sterility, and its relatively short height, and its growth habit that lacks spreading roots.

2 Drawing Sheets

Botanical classification: *Salvia* hybrid.
Variety denomination: 'Amistad'.

BACKGROUND OF THE INVENTION

The present invention relates to a new and distinct cultivar of *Salvia* of hybrid origin and will be referred to hereafter by its cultivar name, 'Amistad'. 'Amistad' is an herbaceous perennial grown for landscape use.

'Amistad' was discovered by one of the Inventors as a naturally occurring whole plant mutation in February of 2007 in a garden bed in Lanús, Buenos Aires province, Argentina. The new cultivar is believed to be a hybrid of unnamed plants of *Salvia gaurantica* and *Salvia gesnerifolia* based on the characteristics of the new cultivar and their proximity to the discovered plant. The exact parents are unknown.

Asexual reproduction of the new cultivar was first accomplished by one of the Inventors by vegetative stem cuttings in June 2010 in Hereford, United Kingdom. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Amistad' as a unique cultivar of *Salvia*.

1. 'Amistad' exhibits flowers that are mauve purple in color.
2. 'Amistad' commences bloom early in the season.
3. 'Amistad' exhibits a long blooming habit with new shoots producing flowers throughout the summer.
4. 'Amistad' has been observed to be sterile.
5. 'Amistad' has been observed to lack spreading roots.
6. 'Amistad' reaches a height of about 1 meter.

'Amistad' can be compared to plants of the species that are thought to be the parents. Plants of *Salvia gaurantica* differ from 'Amistad' in commencing bloom later in the season, in having flowers that are blue in color, and in having roots with a more spreading habit. Plants of *Salvia gesnerifolia* differ from 'Amistad' in being taller in height, in having stems that are woodier, in being less cold hardy, in commencing bloom later in the season, and in having flowers that are orange-red in color. 'Amistad' can also be compared to the *Salvia gaurantica* cultivars 'Black and Blue' (not patented) and 'Argentine Skies' (not patented). 'Black and Blue' differs from 'Amistad' in being taller in height, in commencing bloom later in the season, in producing viable seeds, and in having flowers that are blue in color. 'Argentine Skies' differs from 'Amistad' in being taller in height, in commencing bloom later in the season, and in having flowers that are light blue in color.

BRIEF DESCRIPTION OF THE DRAWING

The accompanying colored photographs illustrate the overall appearance and distinct characteristics of an 8 month-old plant of the new *Salvia* as grown in a two-gallon container in Watsonville, Calif.

The photograph in FIG. 1 provides a view of 'Amistad' in bloom.

Figure 1:
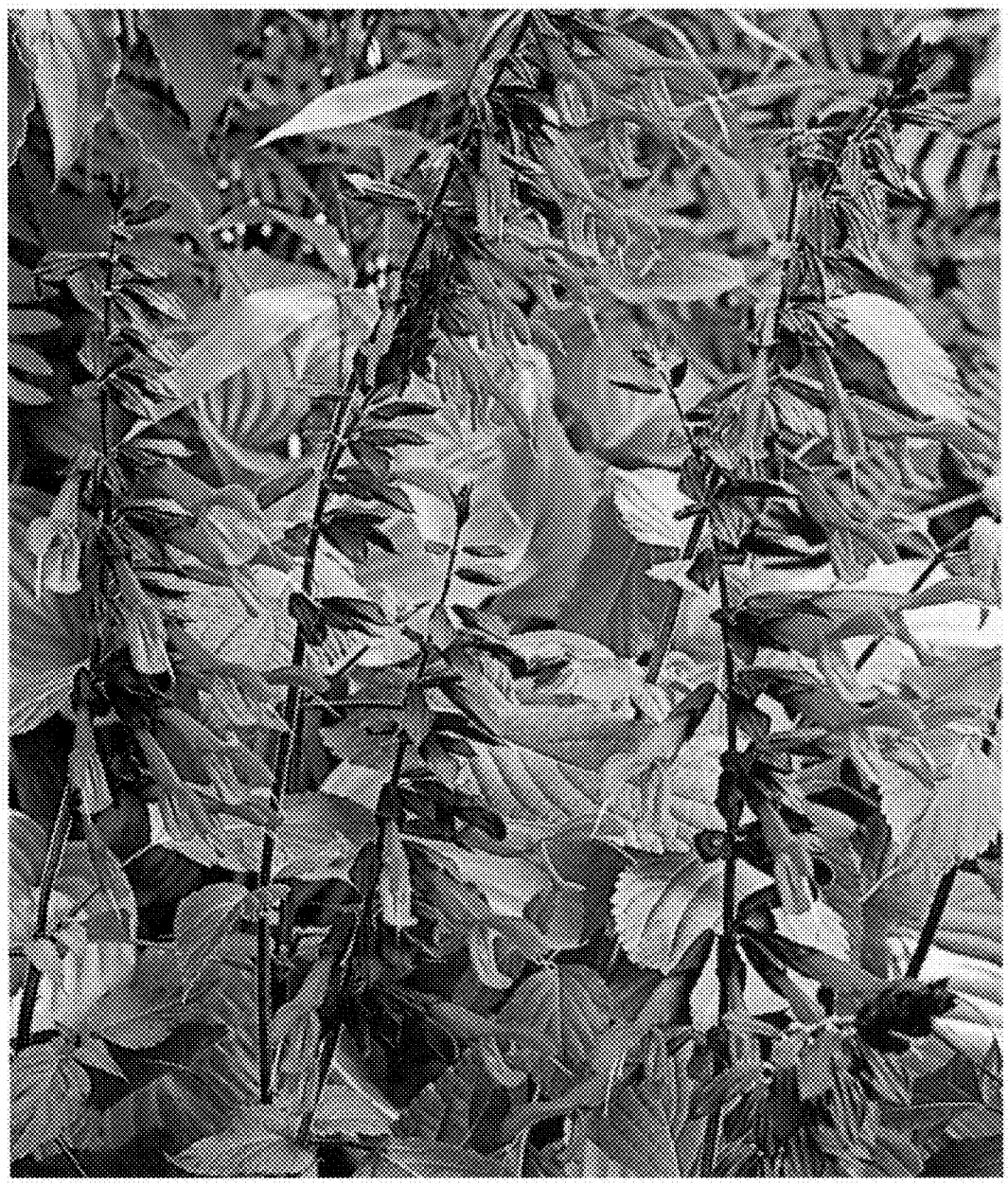
Figure 2:
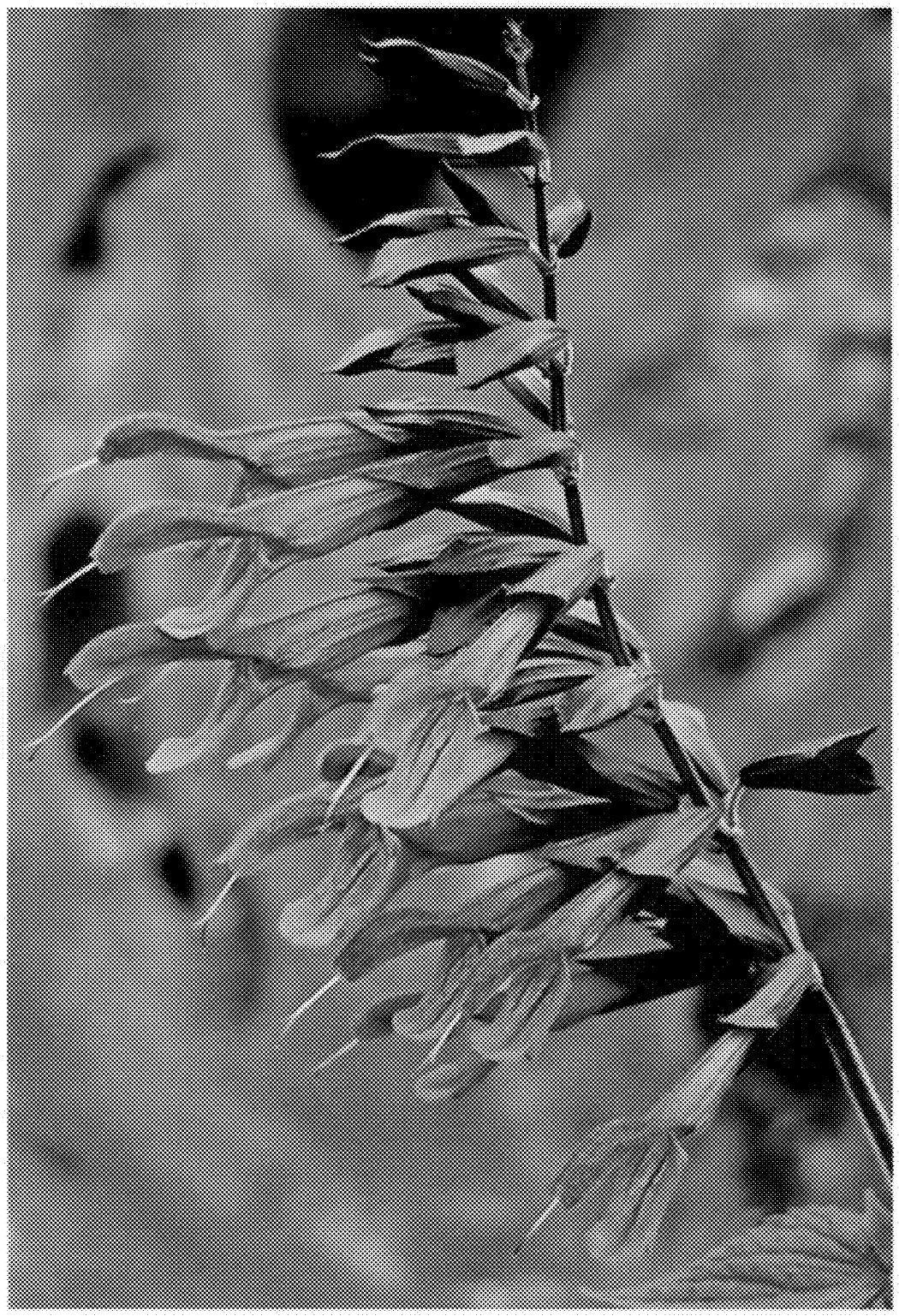

The photograph in FIG. 2 provides a close-up view of an inflorescence of 'Amistad'.

The colors in the photographs may differ slightly from the color values cited in the detailed botanical description, which accurately describe the colors of the new *Salvia*.

DETAILED BOTANICAL DESCRIPTION

The following is a detailed description of the new cultivar of plants grown for 8-months from liner in two-gallon containers in full sun in Watsonville, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Late May to at least late September in Hereford, United Kingdom.

*Plant type.*—Herbaceous perennial.

*Plant habit.*—Upright, well-branched, non spreading.
*Plant size.*—Reaches about 1 m in height and 76 cm in spread without pinching.
*Cold hardiness.*—At least to temperatures of 17° F.
*Diseases and pests.*—No susceptibility or resistance to diseases or pests has been observed.
*Root description.*—Fibrous, non-spreading.

Growth and propagation:
*Propagation.*—Vegetative stem cuttings.
*Growth rate.*—Moderately vigorous.

Stem description:
*Shape.*—4-angled.
*Stem color.*—New growth; 145B suffused with N77A, mature stems; 144A with striations of 144B becoming bark-like at base 148A with striations of 197D.
*Stem size.*—Stem base; about 2.5 cm in diameter, main stems; an average of 1 cm in diameter and 50 cm in length, lateral branches; average of 5 mm in diameter and an up to 27 cm in length.
*Stem surface.*—New growth; pubescent, mature stems; sparsely covered with glandular hairs, base of stem; fissured (bark-like).
*Internode length.*—3 cm between branches and between leaves.
*Branching.*—Average of 3 main stems, an average of 10 lateral braches per stem, an average of 6 sub-lateral flowering branches per lateral branch.

Foliage description:
*Leaf shape.*—Ovate.
*Leaf division.*—Simple.
*Leaf base.*—Broadly cuneate.
*Leaf apex.*—Acuminate.
*Leaf fragrance.*—Mint-like.
*Leaf venation.*—Pinnate, 144B in color on upper surface, 147C in color on lower surface.
*Leaf margins.*—Serrated.
*Leaf arrangement.*—Opposite.
*Leaf attachment.*—Petiolate.
*Leaf surface.*—Glabrous and dull on upper surface and lower surface.
*Leaf size.*—Up to 4.5 cm in length and 3.4 cm in width.
*Leaf color.*—Newly expanded leaves; upper surface 137B and 144A near base, lower surface 147B, mature leaves; upper surface a blend of 137A to N137A, lower surface 147B.
*Petioles.*—Up to 2.2 cm in length and 1.5 mm in width, 144A in color, puberulent surface.

Inflorescence description:
*Inflorescence type.*—Terminal branched raceme of bilabiate flowers.
*Lastingness of inflorescence.*—Individual flowers about 5 days on a plant in a container or in the garden, not persistent.
*Inflorescence size.*—An average of 10 cm in length and 6 cm in width.
*Flower type.*—Tubular-bilabiate.
*Flower number.*—An average of 25 per inflorescence.
*Flower fragrance.*—None.
*Flower buds.*—Tubular in shape, about 2 cm in length and 8 mm in diameter, a blend of N186B and N189A in color (calyx portion) with apex 93A.
*Flower size.*—About 6 cm in length (including extended pistil) and about 1 cm in diameter.
*Peduncle.*—An average of 14 cm in length and 2 mm in width, a blend of N186B and N189A in color, surface is densely covered with glandular hairs, flower internode length an average of 7 mm.
*Pedicels.*—About 6 mm in length and 1 mm in width, N189B in color, surface is pubescent.
*Calyx.*—Tubular, about 1.5 cm in length and 1 cm in width, persistent for about a week after petals drop.
*Sepals.*—2, fused at base with very apex free that is triangular in shape, 5 mm in length and width, apex mucronate, entire margin, a blend of N186B and N189A in color, surface is finely puberulent and lustrous.
*Petals.*—2, arranged in 2 lips fused into tube at base, tube; about 3 cm in length and 8 mm in width, 86B in color with very base NN155C, lustrous surface, upper lip; held upright to tube and slightly protruding outward, curved into renal shape around pistil and stamens, about 1.5 cm in length and 5 mm in width, 86B in color with very base NN155C, velvety on outer surface and lustrous on inner surface, apex single notched, base fused to tube, lower lip; oval in shape with sides recurved, margin entire, apex 2 notched, base fused, surface velvety on upper surface and lustrous on lower surface, about 1.2 cm in length and 7 mm in width, a blend of N186B and N189A in color on outer and inner surface with central area (crest-like) on inner surface suffused with N87D.

Reproductive organs:
*Gynoecium.*—1 pistil, about 5 cm in length with about 1 cm exserted beyond corolla, style is about 4.6 cm in length, 0.8 mm in width and NN155B in color with very apex 86B with hairs 86B in color, stigma is bifid with arms about 3 mm in length, linear in shape and 86A in color, ovary is superior, oblong in shape, about 3 mm in length and 2 mm in diameter and 158A in color.
*Androcoecium.*—2 stamens, filaments are 85B in color, about 1.8 cm in length and 0.8 mm in width, attached to lobe sides with linear arms about 2.5 mm in length and 85B in color with base N89A, fused at base, anthers are about 3 mm in length, N89A in color and dorsifixed, pollen is abundant in quantity and about 159B in color.
*Fruit and seed.*—Observed to be sterile with no viable seeds formed.

It is claimed:

1. A new and distinct cultivar of *Salvia* plant named 'Amistad' as herein illustrated and described.

* * * * *